United States Patent
Gonzalez et al.

(10) Patent No.: US 7,814,673 B2
(45) Date of Patent: Oct. 19, 2010

(54) ANIMAL VEST SIZING DEVICE AND METHOD

(75) Inventors: Elias L. Gonzalez, Fayetteville, NC (US); Tyler A. Cigard, Fayetteville, NC (US)

(73) Assignee: Eagle Industries Unlimited, Inc., Fenton, MO (US)

( * ) Notice: Subject to any disclaimer, the term of this patent is extended or adjusted under 35 U.S.C. 154(b) by 45 days.

(21) Appl. No.: 12/369,557

(22) Filed: Feb. 11, 2009

(65) Prior Publication Data

US 2010/0199507 A1    Aug. 12, 2010

(51) Int. Cl.
*G01B 5/02*    (2006.01)

(52) U.S. Cl. .......................................................... 33/511

(58) Field of Classification Search .................... 33/511, 33/512, 514.2, 2 R, 17 R, 756, 755
See application file for complete search history.

(56) References Cited

U.S. PATENT DOCUMENTS

| | | | | |
|---|---|---|---|---|
| 633,654 | A | * | 9/1899 | Melick ............................ 33/15 |
| 2,017,813 | A | * | 10/1935 | Giuntini ........................ 33/3 B |
| 3,327,394 | A | * | 6/1967 | Tenteris ......................... 33/2 R |
| 3,832,780 | A | * | 9/1974 | Lewis ............................ 33/2 R |
| 4,355,600 | A | | 10/1982 | Zielinski |
| 4,868,990 | A | * | 9/1989 | Steinberg ........................ 33/15 |
| 4,974,331 | A | * | 12/1990 | Watterson ................... 33/514.2 |
| 5,060,458 | A | | 10/1991 | Curtis |
| 5,068,921 | A | | 12/1991 | Jones |
| 5,163,272 | A | | 11/1992 | Finley et al. |
| D372,563 | S | | 8/1996 | Waugh, Jr. |
| D379,686 | S | | 6/1997 | Caditz |
| D404,852 | S | | 1/1999 | Powell-Lesnick |
| 5,996,537 | A | | 12/1999 | Caditz |
| 6,123,049 | A | | 9/2000 | Slater |
| 6,178,652 | B1 | * | 1/2001 | Foster .......................... 33/511 |
| 6,595,162 | B1 | | 7/2003 | Hibbert |
| 2005/0217609 | A1 | * | 10/2005 | Dorton et al. ................ 119/792 |

FOREIGN PATENT DOCUMENTS

CA    2249186    4/2004

OTHER PUBLICATIONS

Meslosh, Charlie, FBI Law Enforcement Bulletin, Bullerproof dogs, the canine ballistic vest phenomenon—Perspective, Oct. 2002, retrieved Apr. 23, 2008 from http://findarticles.com/p/articles/mi_m2194/is_10_71/ai_93915938/print, 3 pps.

(Continued)

*Primary Examiner*—Christopher W Fulton
(74) *Attorney, Agent, or Firm*—Husch & Blackwell LLP

(57) ABSTRACT

A vest sizing device including a shell member having associated therewith a plurality of rule scales and rule index members that cooperate with one another to provide a plurality of girth dimensions for a four-legged animal by longitudinal position. The shell member when configured for use defines a plurality of openings including a neck opening, an abdominal or rear opening, at least one leg opening, and an access opening.

11 Claims, 3 Drawing Sheets

OTHER PUBLICATIONS

Bullet Proof ME Body Armor, Canine Vests—K-9 Armor web page, retrieved Apr. 23, 2008 from http://www.bulletproof.com/Canine_Vests.shtml, 44 pps.

Diamondback Tactical, K-9 Body Armor web page, retrieved Apr. 28, 2008 from http://www.diamondbacktactical.com/K-9-Body-Armor-P1672C261.aspx, 2 pps.

Signature K-9, promotional items web page, retrieved Apr. 28, 2008 from http://www.signaturek9.com/, 2 pps.

Signature K-9, Military Dog Product Categories web page, retrieved Apr. 28, 2008 from http://www.signaturek9.com/military-do-harness/k-9-body-armor—pga3a-(various-sizes-colors)-79, 3 pps.

Pointblank Body Armor Inc, Measuring your dog for the K-9 Operations vest, web page, retrieved Apr. 28, 2008 from http://www.pointblankarmor.com, 1 pp.

Signature K-9, Signature K-9 Innovative Equipment for the future catalog, retrieved Apr. 28, 2008 from http://www.signaturek9.com, 60 pps.

PointBlank Body Armor, Inc., K-9 Operations Vest web page, retrieved Apr. 28, 2008 from http://www.pointblankarmor.com/k9opvest.asp, 2 pps.

K9 Storm Incorporated, K9 Storm Catalogue, The Aerial Insertion Vest web page, retrieved Apr. 28, 2008 from http://k9storm.com/cataloguenew4.html, 2 pps.

K9 Storm Incorporated, Vest Features web page, retrieved Apr. 28, 2008 from http://k9otrm.com/tech.html, 4 pps.

K9 Storm Incorporated, K9 Storm Catalogue, The Assault Vest web page, retrieved Apr. 28, 2008 from http://k9storm.com/cataloguenew3.html, 22 pps.

K9 Storm Incorporated, K9 Storm Catalogue, The Patrol-Swat Series web page, retrieved Apr. 28, 2008 from http://k9storm.com/cataloguenew1.html, 2 pps.

K9 Storm Incorporated, news web page, K9 Storm Vest Save Auburn PD k9 "Blitz"!, Jul. 7, 2003, retrieved Apr. 28, 2008 from http://k9storm.com/news3.html, 4 pps.

Associated Press, Police dog nabs fleeing gunman in Auburn, Jul. 7, 2003, retrieved Apr. 28, 2008 from http://king5.com/localnews/stories/NW_070703WABpolice_dogPL.66002402.html, 1 pp.

K9 Storm Incorporated, Mission Statement web page, retrieved Apr. 28, 2008 from http://k9storm.com/profile.html, 2 pps.

CC Digital Dog, Search Dog Law Enforcement Support Dog web page, retrieved Apr. 23, 2008 from http://www.ccdogduds.com/id23_law_enforcement_parade_vest.htm, 1 pp.

CC Digital Dog, Search Dog Law Enforcement Support Dog web page, retrieved Apr. 23, 2008 from http://www.ccdogduds.com/id23_m.htm, 8 pps.

CC Digital Dog, Site Directory web page, retrieved Apr. 23, 2008 from http://www.ccdogduds.com/id24_1.htm, 2 pps.

CC Digital Dog, K9 Lifeline web page, retrieved Apr. 23, 2008 from http://www.ccdogduds.com/id24_m.htm, 2 pps.

50 Degree Company, Working Canines & Pets, New Cooling Technology Reduces The Health Risks Associated with Hest Stress! web page, retrieved Apr. 23, 2008 from http://www.50degree.com/custom/index.cfm?ID=42464, 3 pps.

* cited by examiner

US 7,814,673 B2

ANIMAL VEST SIZING DEVICE AND METHOD

BACKGROUND OF INVENTION

Canines oftentimes wear garments for a wide variety of reasons. One such garment is a vest. Vests are oftentimes utilized by canines (hereinafter referred to as a dog for convenience) in military and law enforcement applications such as search and rescue, drug enforcement and other civil and criminal applications. Such vests are oftentimes used to allow a dog to carry supplies and/or equipment, to be hoisted and/or carried by a handler, or even parachute with a handler into the area of investigation with the vest being used to attach the dog temporarily to the handler. The vest may also be used to provide armor protection for the dog in combat zones or in certain law enforcement applications. Currently, such vests are provided in general fixed sizes (e.g. small, medium, large) and/or with size adjusting means like adjustable straps. However, these sizing means have not been totally effective to provide proper fit and proper functioning of a vest particularly in harsh use conditions. Additionally, adjustable vests require adjustment devices that add to the manufacturing cost and can make the vest functionally less reliable. Still further, and importantly, many animals and most notably dogs have widely varying girth dimensions depending upon the type and size of the dog as well as varying length dimensions making fitting a garment difficult and unreliable.

The present invention solves the aforementioned problems by providing a sizing garment that reliably provides girth measurements of a dog or other animal at predetermined longitudinal positions along the length of the dog or other animal to allow making custom sized garments.

SUMMARY OF INVENTION

The present invention relates to a device for sizing a dog or other animal for a vest. The present device includes a shell member having portions defining a neck opening, at least one leg opening and an abdominal opening. The shell member also has an access opening extending between the neck and abdominal openings. The present sizing device includes a plurality of transversely or circumferentially extending rows of girth dimension indicia forming rule scales. The present device also includes a plurality of rule index members operably associated with the shell member which extend transversely of the outer shell, each rule index member cooperating with a respective rule scale to indicate a girth dimension at a predetermined longitudinal position along the length of the dog or other animal.

The present invention also relates to a method of sizing a dog or other animal for a garment such as a vest. The method includes placing a plurality of rule index members substantially simultaneously on a dog or other animal to be sized each at a respective position along the length of the torso. The longitudinal positions for each girth measurement are longitudinally fixed. The rule index members are positioned transversely of the dog or other animal, each in indexed relation to a respective rule scale with girth dimension indicia associated therewith. The plurality of girth dimensions as measured are recorded by longitudinal position. The girth dimensions are then transferred to a garment manufacturer that uses the girth dimensions to construct a custom fit garment.

BRIEF DESCRIPTION OF DRAWINGS

Like numbers throughout the various Figures designate like or similar parts and/or construction.

DETAILED DESCRIPTION

Figure 1:
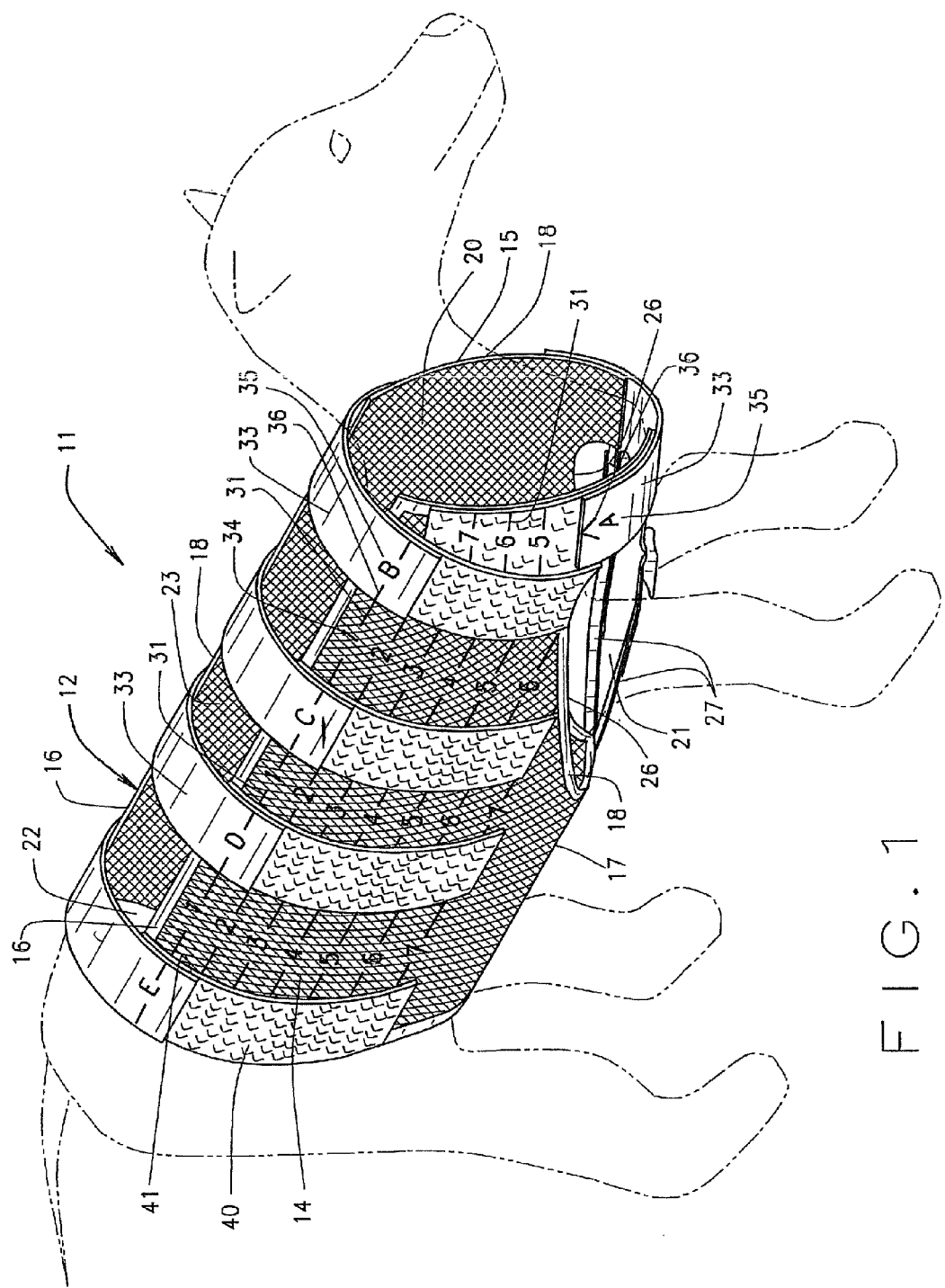
FIG. 1 is a perspective view of a device for sizing a canine or other animal for a garment.

The reference numeral 11 designates generally a device for sizing a garment for a four-legged animal like a canine and, in particular, a dog. The term dog is used hereinafter for convenience sake only and the subject device may apply to other animals. The sizing device 11 includes a shell member 12 having side panel portions 14, 15 and top and bottom panel portions 16, 17. The shell member 12 is designed for extending around the girth of a dog or other animal and along the length of the dog for releasable mounting on a dog. The shell member 12 may be made of any suitable material as, for example, an open weave mesh, or a woven or knit fabric. The fabric may be made from natural or synthetic fiber or a combination thereof. The edge portions of the shell member may be bound for example by stitching and/or using a sewn tape 18 to bind the edges. Binding of the edges can be done to prevent unraveling of the shell member fabric.

Figure 3:
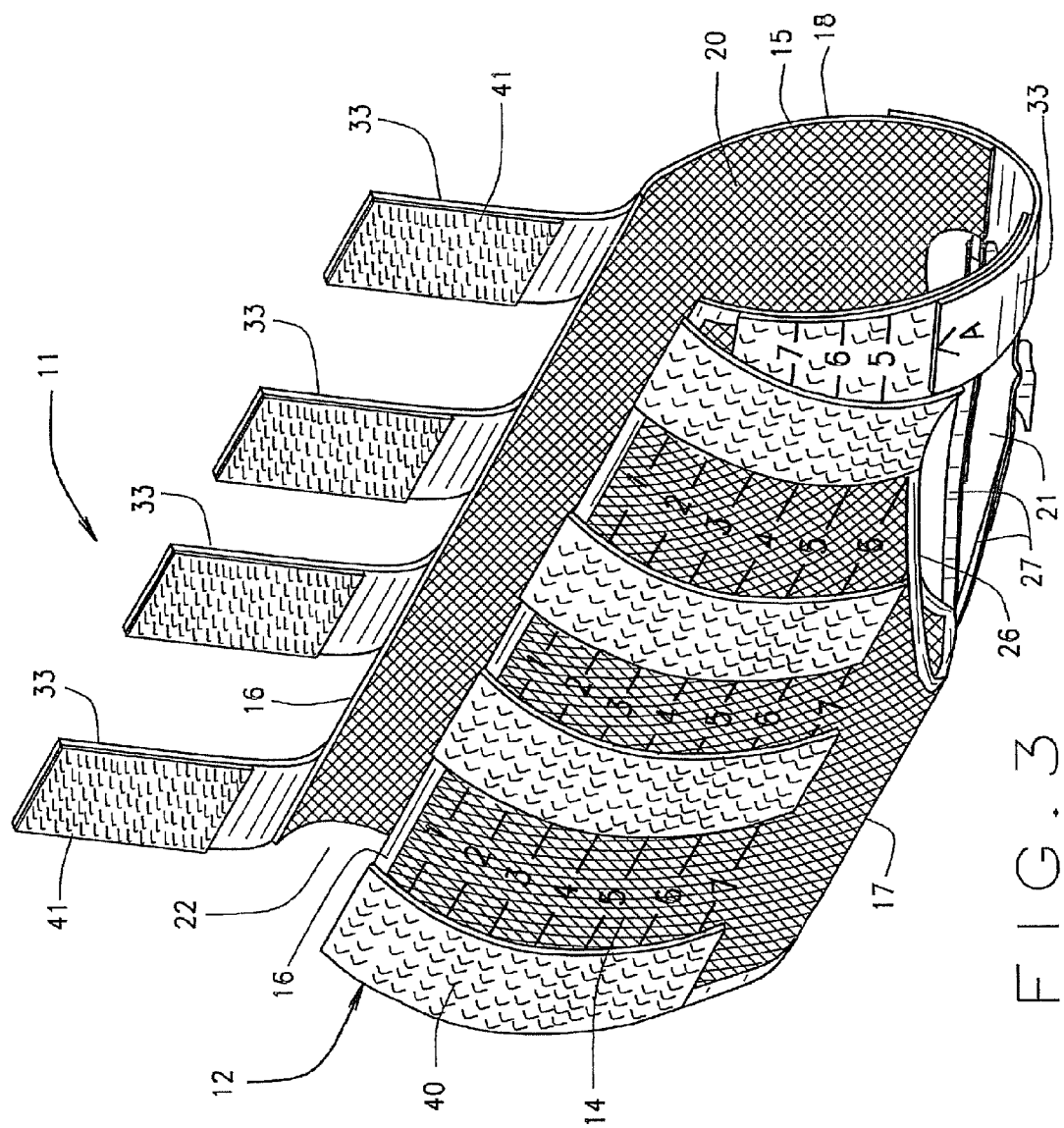
FIG. 3 is a perspective view of the device of FIG. 1 with portions shown in an unfastened configuration to illustrate the detail thereof.

The shell member 12 includes edge portions defining a neck opening 20, portions of at least one leg opening 21 and an abdominal or rear opening 22 (FIG. 3). It is preferred that the neck opening 20 and the leg opening 21 be separate openings as illustrated in FIG. 1. An access opening 23 is also provided and may extend between the neck opening 20 and the abdominal or rear opening 22 to provide a means for ingress and egress for the dog to facilitate mounting and removal of the device 11 on a dog or other animal. As shown, the neck opening 20, abdominal opening 22 and access opening 23 are defined by perimeter edge portions of the shell member 12 when the shell member is in a closed configuration as best illustrated in FIGS. 1 and 3. In a preferred embodiment, there are two leg openings 21. The leg openings 21 are formed by a shell edge portion 26 and a respective strap 27. The size of the shell member 12 will be established by the size range of the dogs or other animals to be measured. It is recognized and anticipated that the access opening 23 may be positioned and located anywhere between the neck and rear openings 20 and 22 including extending the full length therebetween as illustrated in FIG. 1.

The measuring device 11 includes means for measuring girth by measuring multiple circumferences of the dog transversely at predetermined positions along the length of the dog. In a preferred embodiment, at least three girth dimensions are to be measured, one (at A) adjacent or in the vicinity of the neck area of the dog, one (at E) adjacent or in the vicinity of the rear of the abdomen of the dog, and one (at B) adjacent the chest area of the dog. The measuring means in the illustrated structure includes at least one and preferably a plurality of transversely or circumferentially extending rule scales 31 with one or more rows of girth dimension indicia 34 thereon. There is also provided a plurality of rule index members 33 associated with the shell member 12 and extend transversely of the shell 12. The rule index members 33 are each movable relative to a respective scale 31. Each of the rule index members 33 cooperates with a respective rule scale 31 to indicate a girth measurement at the respective longitudinal position associated with that particular rule scale 31. In the illustrated structure, the rule scales 31 have dimension scale indicia 34 on the shell member. In the illustrated embodiment, a rule index member 33 includes a transversely extending strap in longitudinally spaced apart relationship from other rule index members between the neck opening 20 and the abdominal opening 22. The neck opening 20 and the leg opening 21 are preferably separated by a rule index member 33 at A when a neck dimension is to be taken. The cooperation between a rule index member 33 and a respective girth rule scale 31 indicates a girth dimension at a specific location longitudinally of the dog. The scale indicia 34 may be an actual dimension, for example, inches or an arbitrary scale. Indicia 35 may also be provided to designate which scale 31 is being read. A coordinating scale indicator 36 is provided to be positioned adjacent a rule scale 31 to indicate the respective girth dimension at that location. Although FIG. 1 illustrates a plurality of rule scales 31 extending along the longitudinal length of the shell member 12, it is recognized and anticipated that a single rule scale 31 could be used and could extend along an appropriate portion of the longitudinal length of the shell member 12 and any suitable number of rule index members 33 could cooperate with the single rule scale 31 at various longitudinal locations therealong to produce a plurality of girth measurements.

Figure 2:
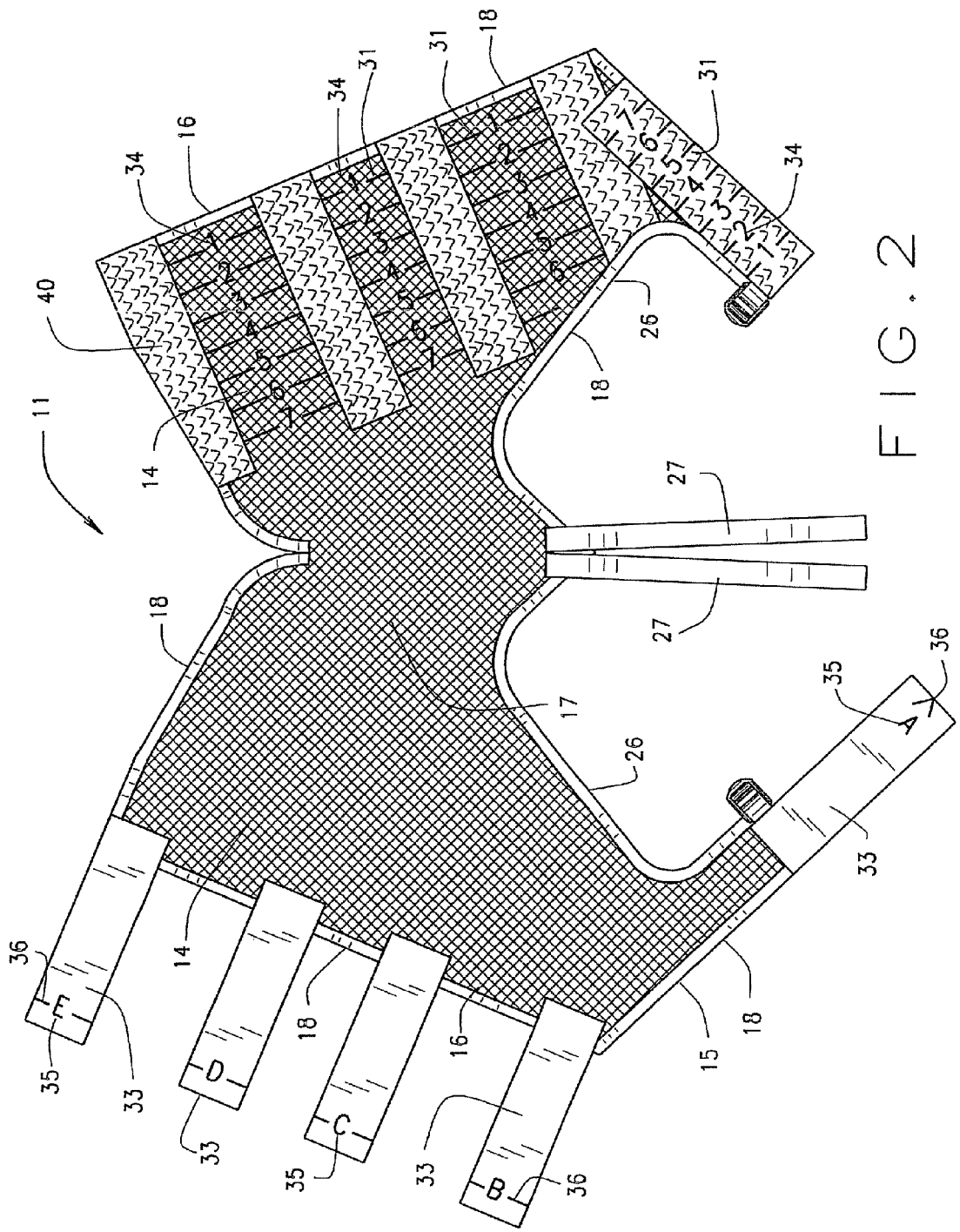
FIG. 2 is an outside plan view of the device of FIG. 1 shown in a flat configuration.

In the illustrated structure, the indicia 34 are carried by the shell member 12 and the indicators 36 are each carried by a respective rule index member 33. As shown, the rule index members 33 are in the form of straps. It is noted that the indicia 34 may be provided on the rule index members 33 and the indicator 36 may be provided on the shell member 12. It is also recognized and anticipated that a single indicator 36 attachable to each rule index member 33, or slidable across the device 11, or pivotable preferably at a central location on the shell member 12 to each rule scale 31 may be used in accordance with the teachings of the present invention to obtain the necessary girth dimensions, or a separate indicator device 36 associated with each rule index member 33 may be used with the present device 11 as illustrated in FIG. 2. The scales 31 and rule index members 33 cooperate to provide a girth dimension at each of the plurality of measurement locations along the length of the shell member 12 and along the length of the dog on which the shell member 12 is mounted. The longitudinal positions of each of the size indicators is fixed to provide consistently positioned longitudinal locations for the girth dimensions.

In a preferred embodiment, there are at least three girth measuring means positioned along the length of the device 11 and, as illustrated in FIG. 1, there are five measuring means denoted as A, B, C, D and E. Any suitable plurality of girth measuring means may be provided. The forward most measuring device (denoted as A) measures the neck circumference, the next in line measuring device (denoted B) measures the chest girth, and so on until the final measuring device (denoted E) measures the rear abdomen of the dog.

While straps 33 can be attached to the shell member as by sewing, other devices can be used instead of straps for the rule index members 33. For example, a single transparent member can be used in place of multiple straps. Preferably, the shell member 12 and the rule scales 31 and rule index members 33 are substantially nonstretchable to provide consistent readings irrespective of any reasonable tension placed on the various components.

The present invention is better understood by description of the method of use. The access opening 23 is allowed to be opened by detaching the rule index members 33 (when secured in place) from the shell member 12. This attachment and detachment may be made by hook and loop fastener elements 40, 41 to provide for releasable securement. Disengaging the fastening elements 40, 41 from one another opens the access opening 23. The dog's head is placed in the neck opening 20 area and the dog's front legs are placed in the leg openings 21. The shell member 12 is then wrapped around the torso portion of the dog between the front and rear legs and the rule index members 33 and their respective scale indicators 36 are aligned with a respective row of girth dimension indicia 34 associated with a respective rule scale 31. Each rule index member 33 is then used to snug the shell member 12 around the dog's torso and the attachment member 40 associated with each rule index member 33 is reattached to its corresponding attachment member 41 aligning each scale indicator 36 with a respective rule scale 31. After taking the dimensions by matching an indicator 36 with the girth dimension 34 associated with each rule scale 31, the girth dimension values may be recorded by longitudinal positions (e.g. A, B, . . . E) and transferred to a garment manufacturer to manufacture a garment that is custom made for the particular dog. The girth dimensions can be used to determine the perimeter/circumference parameters of a vest shell after which the vest shell can be used to make a custom sized vest. The dimensions taken by the present invention at the respective longitudinal positions along the shell member 12 and along the dog's torso are consistent both in girth or circumference measurements and in longitudinal position location. The garment manufactured can be a vest or any other suitable garment which can benefit from multiple girth dimensions for custom sizing.

Thus, there has been shown and described several embodiments of a novel invention. The terms "having" and "including" and similar terms as used in the foregoing specification are used in the sense of "optional" or "may include" and not as "required". Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A device for sizing a canine for a garment, the device comprising:
    a shell member including;
        portions defining a neck opening, at least one leg opening and an abdominal opening, said shell member having an access opening extending between the neck and abdominal openings;
        at least one transversely extending rule scale having girth dimension indicia, said at least one transversely extending rule scale being on the shell member; and
        a plurality of scale indicators operatively associated with the shell member at spaced apart locations along the longitudinal length of said shell member, each scale indicator cooperating with said at least one rule scale to indicate a girth dimension at a respective longitudinal position along the length of said shell member, said scale indicators being positioned between the neck opening and abdominal opening.

2. The sizing device of claim 1 wherein the scale indicators each being on at least one rule index member.

3. The sizing device of claim 2 wherein the at least one rule index member includes a plurality of spaced apart transversely extending straps positioned between the neck and abdominal openings.

4. The sizing device of claim 3 wherein each strap includes a respective scale indicator to associate with a respective row of said girth dimension indicia, each said respective scale indicator indicating a respective girth dimension.

5. A device for sizing a canine for a garment, the device comprising:
- a shell member including;
    - portions defining a neck opening, at least one leg opening and an abdominal opening, said shell member having an access opening positioned between said neck and abdominal openings;
    - a plurality of transversely extending rule scales each having girth dimension indicia associated therewith, said transversely extending rule scales being located on the shell member, said plurality of rule scales being spaced apart longitudinally along the length of said shell member; and
    - at least one scale indicator operatively associated with said shell member, said at least one scale indicator cooperating with a rule scale at respective longitudinal positions along said shell member to indicate a girth dimension at each said respective longitudinal position along said shell member.

6. The sizing device of claim 5 including a plurality of scale indicators, each scale indicator cooperating with a respective one of said rule scales to indicate a girth dimension at a respective longitudinal position along said shell member.

7. The sizing device of claim 6 wherein each of said plurality of scale indicators are associated with a respective one of a plurality of rule index members.

8. The sizing device of claim 7 wherein each of said rule index members comprises a transversely extending strap positioned between said neck and abdominal openings.

9. A method of sizing a canine for a garment, the method including:
- placing a shell member on a canine, said shell member having a plurality of rule scales on the shell member and a plurality of scale indicators associated therewith;
- placing a plurality of said scale indicators each at a respective position along a portion of the length of a canine;
- associating each said scale indicator with a respective one of said rule scales, each rule scale having girth dimension indicia;
- measuring a plurality of girth dimensions by the alignment of a scale indicator with a respective girth dimension indicia; and
- recording the girth dimension indicia by longitudinal position.

10. The method of claim 9 including cutting a perimeter of a vest shell utilizing said measured girth dimensions.

11. The method of claim 10 including forming a vest using the cut vest shell.

* * * * *